United States Patent
Vickers

(10) Patent No.: US 11,311,383 B2
(45) Date of Patent: Apr. 26, 2022

(54) SPINAL IMPLANT SYSTEM AND METHOD

(71) Applicant: WARSAW ORTHOPEDIC, INC., Warsaw, IN (US)

(72) Inventor: Scott M. Vickers, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 154 days.

(21) Appl. No.: 16/525,181

(22) Filed: Jul. 29, 2019

(65) Prior Publication Data

US 2019/0350714 A1 Nov. 21, 2019

Related U.S. Application Data

(63) Continuation of application No. 15/052,605, filed on Feb. 24, 2016, now Pat. No. 10,383,731.

(51) Int. Cl.
| | |
|---|---|
| *A61F 2/28* | (2006.01) |
| *A61L 27/56* | (2006.01) |
| *A61L 27/14* | (2006.01) |
| *A61L 27/36* | (2006.01) |
| *A61L 27/54* | (2006.01) |
| *A61F 2/30* | (2006.01) |

(52) U.S. Cl.
CPC ............ *A61F 2/2846* (2013.01); *A61L 27/14* (2013.01); *A61L 27/3608* (2013.01); *A61L 27/54* (2013.01); *A61L 27/56* (2013.01); *A61F 2002/30467* (2013.01); *A61F 2310/00359* (2013.01); *A61L 27/365* (2013.01); *A61L 2300/414* (2013.01); *A61L 2430/38* (2013.01)

(58) Field of Classification Search
CPC ................................................... A61F 2/2846
See application file for complete search history.

(56) References Cited

U.S. PATENT DOCUMENTS

| | | | |
|---|---|---|---|
| 2,788,935 A | * | 4/1957 | Cockrell, Jr. .......... B65D 27/12 383/35 |
| 4,646,795 A | | 3/1987 | Hebron et al. |
| 5,202,021 A | | 4/1993 | Griffin et al. |
| 5,353,531 A | | 10/1994 | Doucette |
| 5,716,087 A | | 2/1998 | Backich et al. |
| 5,738,399 A | | 4/1998 | Mitchell |
| 6,294,187 B1 | | 9/2001 | Boyce et al. |
| 6,440,444 B2 | | 8/2002 | Boyce et al. |

(Continued)

FOREIGN PATENT DOCUMENTS

| | | |
|---|---|---|
| CN | 1819806 A | 8/2006 |
| JP | 2001-527437 A | 12/2001 |

(Continued)

OTHER PUBLICATIONS

Office Action dated Nov. 30, 2020, issued by the Japan Patent Office in corresponding Japanese application No. JP 2018-543600. English translation provided.

(Continued)

*Primary Examiner* — Suba Ganesan
(74) *Attorney, Agent, or Firm* — Sorell, Lenna & Schmidt, LLP

(57) ABSTRACT

A delivery system comprising an agent and a foldable covering including a first surface disposed with the agent and a second surface connectable with the first surface to intra-operatively dispose the covering in a selected configuration.

16 Claims, 3 Drawing Sheets

(56) References Cited

U.S. PATENT DOCUMENTS

| | | |
|---|---|---|
| 6,478,825 B1 | 11/2002 | Winterbottom et al. |
| 6,696,073 B2 | 2/2004 | Boyce et al. |
| 6,723,131 B2 | 4/2004 | Muschler |
| 7,083,648 B2 | 8/2006 | Yu et al. |
| 7,097,027 B1 | 8/2006 | Chen |
| 7,191,553 B2 | 3/2007 | Doucette et al. |
| 7,387,507 B2 | 6/2008 | Schuler |
| 8,042,688 B2 | 10/2011 | Parks et al. |
| 8,100,452 B1 | 1/2012 | Homewood |
| 2004/0249471 A1* | 12/2004 | Bindseil ............... A61F 2/4455 623/23.51 |
| 2005/0251267 A1 | 11/2005 | Winterbottom et al. |
| 2005/0283255 A1 | 12/2005 | Geremakis et al. |
| 2006/0052879 A1 | 3/2006 | Kolb |
| 2006/0089721 A1 | 4/2006 | Muhanna et al. |
| 2006/0216323 A1 | 9/2006 | Knaack et al. |
| 2007/0088443 A1 | 4/2007 | Hanssen et al. |
| 2007/0098756 A1 | 5/2007 | Behnam |
| 2007/0110820 A1 | 5/2007 | Behnam |
| 2007/0142916 A1 | 6/2007 | Olson et al. |
| 2007/0191963 A1 | 8/2007 | Winterbottom et al. |
| 2008/0107711 A1 | 5/2008 | Shelokov |
| 2009/0130173 A1 | 5/2009 | Behnam et al. |
| 2009/0192474 A1 | 7/2009 | Wei et al. |
| 2009/0234277 A1 | 9/2009 | Wei et al. |
| 2009/0240255 A1 | 9/2009 | McKay et al. |
| 2010/0203155 A1 | 8/2010 | Wei et al. |
| 2011/0054408 A1* | 3/2011 | Wei ....................... A61B 17/68 604/175 |
| 2011/0071536 A1 | 3/2011 | Kleiner et al. |
| 2011/0152754 A1 | 6/2011 | Cantor et al. |
| 2012/0097556 A1 | 4/2012 | Gascoine |
| 2012/0297902 A1 | 11/2012 | Leventhal et al. |
| 2013/0004559 A1 | 1/2013 | Li et al. |
| 2013/0280303 A1* | 10/2013 | Drapeau ................. A61L 27/14 424/400 |
| 2013/0289621 A1 | 10/2013 | Fulmer et al. |
| 2014/0200676 A1* | 7/2014 | Shimko ................. A61F 2/2846 623/23.52 |
| 2014/0222162 A1 | 8/2014 | Seedhorn |
| 2014/0277570 A1* | 9/2014 | Behnam ................. A61K 47/46 623/23.51 |

FOREIGN PATENT DOCUMENTS

| | | |
|---|---|---|
| JP | 2006-526486 | 11/2006 |
| JP | 2006-526486 A | 11/2006 |
| JP | 2006526486 A | 11/2006 |
| WO | 98/38918 | 9/1998 |
| WO | WO2004108023 A1 | 12/2004 |

OTHER PUBLICATIONS

International Search Report and Written Opinion for PCT/2017/018814, the counterpart application dated Jul. 13, 2017, 13 pages.

Notice of Office Action, China National Intellectual Property Administration, 201780012649.7, dated Jan. 20, 2020.

Extended European Search Report, dated Oct. 16, 2019, issued by the European Patent Office in EP Appl. No. 17757099.1 for Spinal Implant System and Method, filed on Feb. 22, 2017.

European Patent Office Examination Report, European Application No. 17757099.1, Date of dispatch Jun. 16, 2021.

Notice of Allowance dated Jan. 14, 2022 by the Japan Patent Office in corresponding Japanese Application No. 2018-543600. English translation provided.

The Japan Patent Office (JPO), Notice of Reasons for Rejection, Patent Application No. 2021-001306, dated Dec. 3, 2021.

* cited by examiner

SPINAL IMPLANT SYSTEM AND METHOD

FIELD

The present disclosure generally relates to medical devices for the treatment of musculoskeletal disorders, and more particularly to a spinal implant system and a method for treating a spine.

BACKGROUND

Spinal pathologies and disorders such as degenerative disc disease, disc herniation, spondylolisthesis, stenosis, osteoporosis, tumor, scoliosis and other curvature abnormalities, kyphosis and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, microdiscectomy, corpectomy, decompression, laminectomy, laminotomy, foraminotomy, facetectomy and implantable prosthetics. As part of these surgical treatments, spinal constructs including implants, such as, for example, bone graft, bone fasteners, spinal rods and interbody devices can be used to provide stability to a treated region. For example, during surgical treatment, surgical instruments can be used to deliver components of the spinal constructs to the surgical site for fixation with bone to immobilize a joint. This disclosure describes an improvement over these prior technologies.

SUMMARY

In one embodiment, a spinal implant is provided. The spinal implant has an agent and a foldable covering including a first surface disposed with the agent and a second surface connectable with the first surface to intra-operatively dispose the covering in a selected configuration.

BRIEF DESCRIPTION OF THE DRAWINGS

The present disclosure will become more readily apparent from the specific description accompanied by the following drawings, in which.

DETAILED DESCRIPTION

Figure 1:
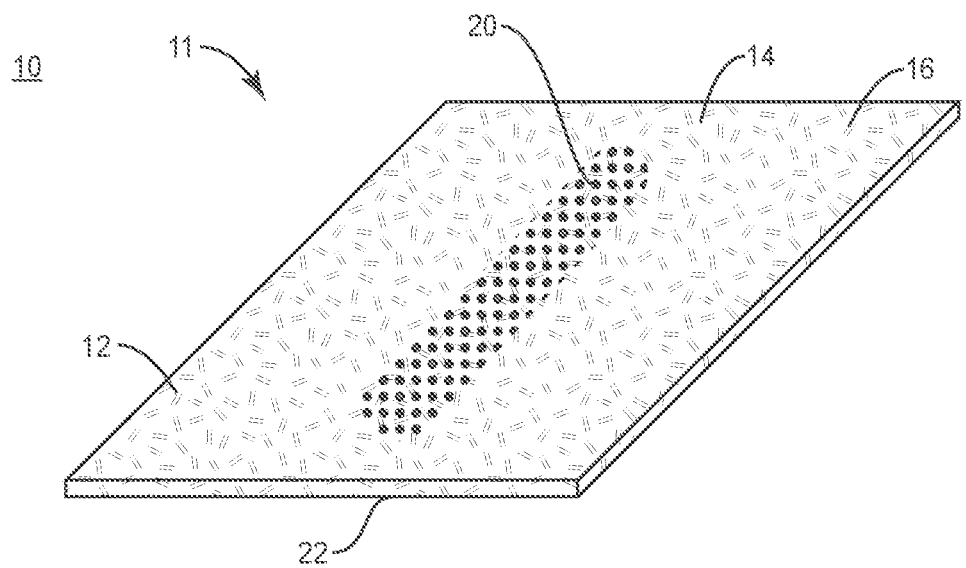
FIG. 1 is a perspective view of components of one embodiment of a system in accordance with the principles of the present disclosure.

The exemplary embodiments of a spinal implant system are discussed in terms of medical devices for the treatment of musculoskeletal disorders and more particularly, in terms of a spinal implant system for treating a spine at a surgical site and a method for treating a spine. In some embodiments, the present system comprises a spinal implant that delivers a substance to the surgical site. In some embodiments, the present system comprises a spinal implant employed with a spinal joint and fusion, for example, with a cervical, thoracic, lumbar and/or sacral region of a spine.

In some embodiments, the spinal implant system includes autologous bone, either from the iliac crest or local bone from decompressions. In some embodiments, the spinal implant system includes retention of autologous bone at the site of implantation. In some embodiments, the spinal implant includes a resorbable porous mesh sheet that incorporates a hook and loop fastener. In some embodiments, the mesh sheet is configured to adhere to itself when folded. In some embodiments, the spinal implant includes a sheet combined with autograft and configured to be folded into a selected implant configuration intra-operatively. In some embodiments, the spinal implant system provides for customization of the spinal implant to meet surgical and/patient needs.

In some embodiments, the spinal implant includes a resorbable porous polymer mesh sheet with hooks on one surface that adhere to the opposite surface of the mesh when the surfaces are folded together. In some embodiments, the spinal implant system includes a spinal implant configured for intra-operative folding into a selected implant configuration to deliver and retain autograft at the site of implantation. In some embodiments, the spinal implant system includes full intra-operative customization of a selected implant configuration to a desired shape and/or volume required.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise. The term bone, as used herein, refers to bone that is cortical, cancellous or cortico-cancellous of autogenous, allogenic, xenogenic, or transgenic origin unless specifically referred to otherwise.

Notwithstanding the numerical ranges and parameters set forth herein, the broad scope of this disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Demineralized, as used herein, refers to any material generated by removing mineral material from tissue, for example, bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of this disclosure. In some embodiments, demineralized bone has less than 95% of its original mineral content. Demineralized is intended to encompass such expressions as "substantially demineralized," "partially demineralized," and "fully demineralized."

Demineralized bone matrix, as used herein, refers to any material generated by removing mineral material from bone tissue. In preferred embodiments, the DBM compositions as used herein include preparations containing less than 5% calcium and preferably less than 1% calcium by weight. Partially demineralized bone (e.g., preparations with greater than 5% calcium by weight but containing less than 100% of the original starting amount of calcium) are also considered within the scope of this disclosure.

Osteoconductive, as used herein, refers to the ability of a non-osteoinductive substance to serve as a suitable template or substance along which bone may grow.

Osteogenic, as used herein, refers to the ability of an agent, material, or implant to enhance or accelerate the growth of new bone tissue by one or more mechanisms such as osteogenesis, osteoconduction, and/or osteoinduction.

Osteoimplant, as used herein, refers to any bone-derived implant prepared in accordance with the embodiments of this disclosure and therefore is intended to include expressions such as bone membrane, bone graft, etc.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

Superficially demineralized, as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

In various embodiments, the spinal implant comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

Figure 2:
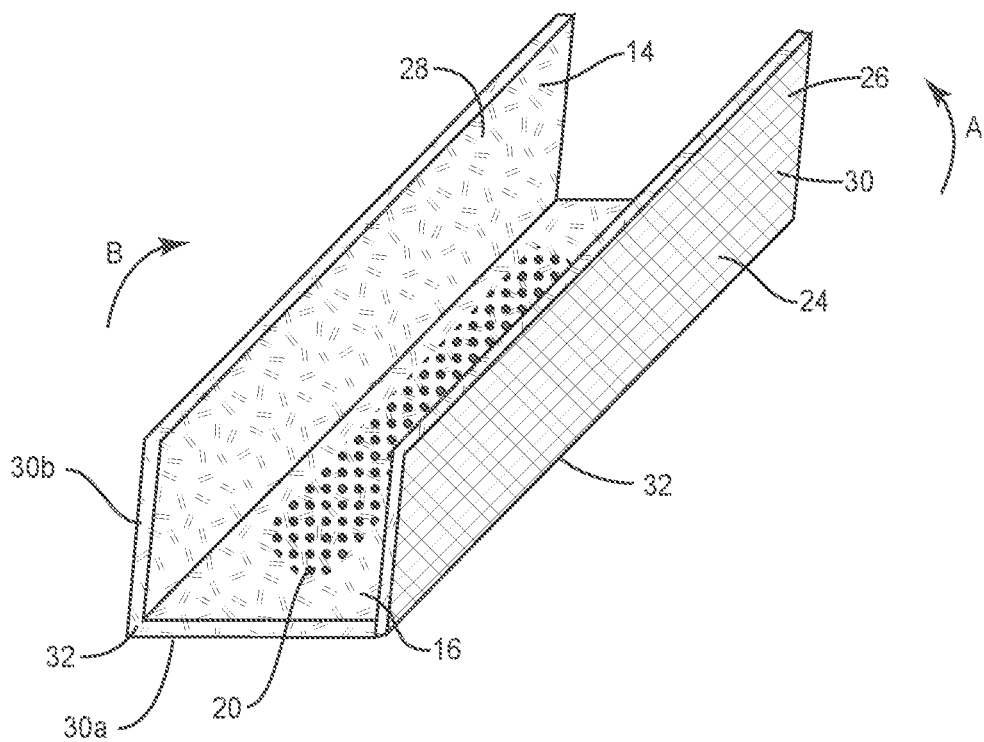
FIG. 2 is a perspective view of the components shown in FIG. 1.
Figure 3:
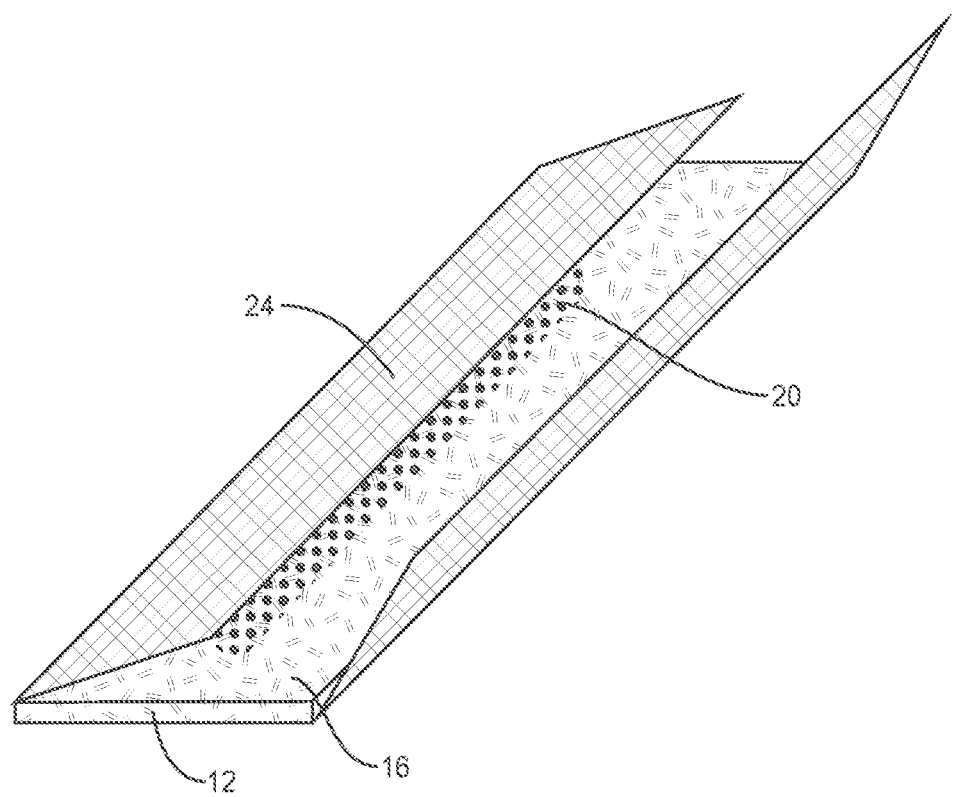
FIG. 3 is a perspective view of the components shown in FIG. 1.
Figure 4:
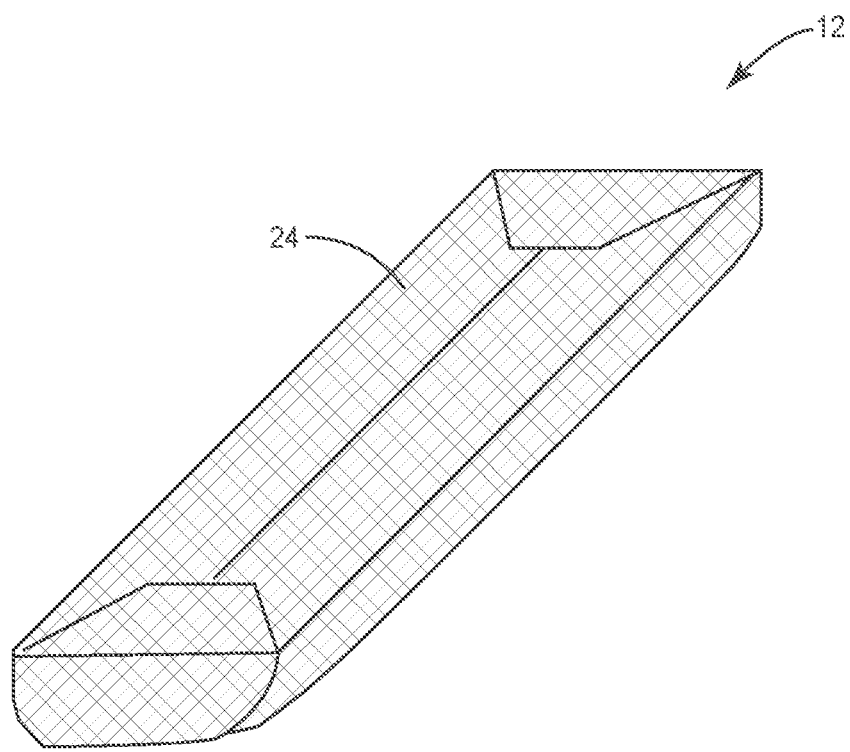
FIG. 4 is a perspective view of the components shown in FIG. 1.
Figure 5:
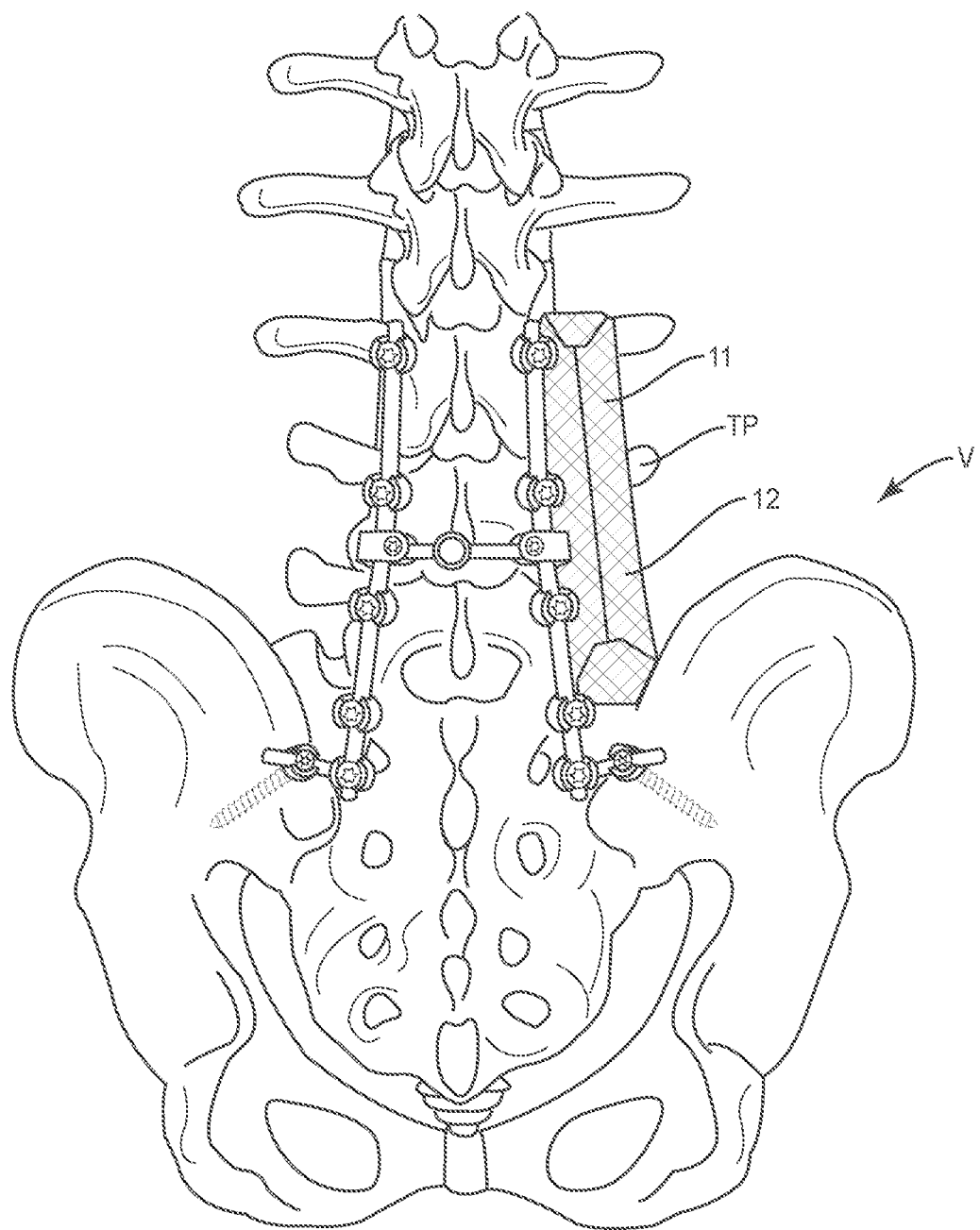
FIG. 5 is a perspective view of components of one embodiment of a system in accordance with the principles of the present disclosure disposed with vertebrae.

In one embodiment, as shown in FIGS. 1-4, an osteogenic spinal implant system 10, similar to the systems, constructs, implants and methods described herein and including the components discussed, comprises a spinal implant 11. Spinal implant 11 includes a foldable covering including a plurality of foldable walls and an agent. The covering includes a first configuration, such as, for example, a flat configuration, as shown in FIG. 1, and is manipulated and/or folded, as shown in FIGS. 2-4, into a selected implant configuration intra-operatively, as shown in FIG. 5.

In some embodiments, the covering may be a temporary covering wherein the covering is substantially resorbable. For example, the covering may be formed of a material that is substantially resorbed within 2 weeks, within 4 weeks, within 12 weeks, or within other suitable time frame. In some embodiments, FIGS. 1-4, an osteogenic spinal implant system 10 including the covering may be a temporary delivery system. In some embodiments, the covering may include one or more attachment mechanisms for retaining spinal implant 11 at the surgical site. The attachment mechanism may be a mechanical attachment mechanism, a physical attachment mechanism, a biological attachment mechanism or a chemical attachment mechanism, or may employ combinations of these. The attachment mechanism may be used to attach the covering to skeletal or soft tissue proximate the surgical site.

In some embodiments, the covering may be used for containment of particulate or morselized materials, optionally to provide a focus or concentration of biological activity. In some embodiments, the covering may be used for containment of a substance one or more of bone particles, bone fibers, other osteoinductive or osteoconductive materials, BMP, antibiotics, or other materials.

In some embodiments, the covering may be used for maintaining materials in spatial proximity to one another, possibly to provide a synergistic effect. In some embodiments, the covering may be used to control availability of an agent provided within the covering to cells and tissues of a surgical site over time.

In some embodiments, the covering may contain an agent such as a graft material. The covering limits, and in some embodiments eliminates, graft migration and maintains graft density. Spinal implant 11 including the agent may be configured to conform to surrounding bony contours or implant space. In some embodiments, spinal implant 11 provides a pathway for healing/cell penetration and tissue ingrowth. Thus, the covering may facilitate transfer or diffusion of materials into and out of the covering. For example, the covering may facilitate diffusion from the covering of an agent provided within the covering or may facilitate diffusion into the covering of materials at the surgical site, such as cells and tissues, into the covering. The covering may be configured to permit diffusion of some agent/materials while substantially preventing diffusion of other agent/materials. Further, in some embodiments, the covering may be configured such that diffusion is permitted into or out of certain portions of the covering but not other portions of the covering.

In some embodiments, the covering may comprise a structural material and, in some embodiments, a functional material. The structural material may comprise a mesh material or a polymeric material. The functional material may comprise, for example, a radiopaque material or a bacteriocidal material. In some embodiments, the covering may be flexible, non-elastic, or elastic. The covering material may be braided, woven, non-woven shape memory, particulate, threaded, porous, non-porous, or substantially solid.

In some embodiments, the covering may participate in, control, facilitate, prevent, or otherwise adjust the release of an agent. For example, the covering may act as a selectively permeable membrane and/or may be porous, with the level of porosity being related to the nature of the agent inside the covering. Thus, the material and configuration of the covering may be selected or adjusted based on desired release characteristics. Specific properties of the structural material that may be adjusted include thickness, permeability, porosity, strength, flexibility, and/or elasticity. In some embodiments, the thickness and porosity of the material may contribute to its strength, flexibility, and elasticity. In some embodiments, the covering may be made of a squishy, moldable, sticky, and/or tacky material to facilitate placement and packing of the covering.

In some embodiments, the covering may be porous to fluid and/or cells, may be biocompatible, and may be resistant to rupture. In some embodiments, the covering may be load-bearing. The covering may be resorbable or non-resorbable. The covering may provide increased handling properties, may have irrigation resistance, may have material retention characteristics, and/or may support cellular penetration. If the covering is made from a resorbable material, the covering degrades and disappears after a period of time. The covering thus may be considered a temporary covering. If the covering is not made of a resorbable material, the covering remains in the body. Tissue ingrowth may occur to bind the host tissue to the agent provided within the covering. Tissue ingrowth through and around the covering, between the host tissue and the agent provided within the covering, may be promoted via openings in the covering.

In some embodiments, the covering may comprise a porous material or a mesh material. The size of the pores of the covering may be designed to permit cellular infiltration (approximately several microns to several millimeters), but may also be designed specifically to exclude cells from the inside of the covering (for example, approximately 0.45 microns) and only allow diffusion of small molecules (proteins and hormones). Thus, the covering may act to control access to the interior of the delivery system by cells. U.S. Patent Application Publication No. 2005/0283255 for Tissue-Derived Mesh for Orthopedic Regeneration describes suitable manners for forming a mesh for use with a covering as provided herein and is herein incorporated by reference in its entirety.

In some embodiments, the covering may include one or more layers, and/or one or more separate sections or compartments. For example, in an embodiment comprising two compartments, one or more agents may be used for the first compartment and a different agent or agents may be used for the second compartment. For example, one compartment or portions thereof may be made of an agent or agents that provide a desired property or properties relative to other compartments or portions thereof, such as increased or decreased resorbability or stiffness, or the different compartments or portions thereof may be imparted with different drug delivery properties. Alternatively, all compartments may comprise the same agent or mixtures of agents. Where the characteristics of the material are varied between compartments or over the surface of a single compartment, the pores of the first compartment or portion thereof may be larger than the pores of the second compartment. In some embodiments, the covering comprises two compartments, first and second agents may be used for the first and second compartments, respectively. The first agent may release or expose a growth factor according to a first rate and the second agent may release a growth factor according to a second rate. Further, the growth factors released by the first and second compartments may be the same or may be different. For example, an angiogenic growth factor may be provided with the first compartment and an osteoinductive growth factor may be provided with the second compartment.

In embodiments comprising more than one compartment, characteristics of the covering material may be varied between compartments. Generally, the porosity, flexibility, strength, or any other characteristic of one compartment may vary from that characteristic of the other compartment.

Further, characteristics of the covering may vary at different positions of the covering regardless of compartmental configuration of the covering.

The covering may be configured for specific compressive strength and rigidity by adjusting density and resorption time of the covering. In some embodiments, a coating may be provided over the covering. For example, the coating may be a compound of poly-L-lactide, of polyglycolic acid, or their polymers, or polyhydroxyalkanoates (polyhydroxybutyrates and polyhydroxyvalerates and copolymers). The coating may be selected such that it has a resorption time wherein it is resorbed by the body and the agent within the covering is permitted to exit through openings in the covering.

In some embodiments, the covering may be fabricated from a polymeric material (for example, see U.S. Pat. Nos. 6,696,073, 6,478,825, 6,440,444, and 6,294,187, 7,985,414 and U.S. Patent Publication No. and 2005/0251267, all herein incorporated by reference in their entirety); woven material and braided material (for example, see U.S. Patent Publication No. 2005/0283255, herein incorporated by reference in its entirety); non-woven materials; shape memory material; porous materials; and non-porous materials may be used. In some embodiments, outer particles may be used to contain inner particles; particles may be attached to threads of material, and/or porosity may be added to mesh fibers. In some embodiments, materials may be used for portions of the covering, such as for a compartment of the covering, that are substantially impenetrable.

In some embodiments, the covering may be formed of a polymer (such as polyalkylenes, for example, polyethylenes, polypropylenes), polyamides, polyesters, poly(glaxanone), poly(orthoesters), poly(pyrolicacid), poly(phosphazenes), polycarbonate, other bioabsorbable polymer such as Dacron or other known surgical plastics, a natural biologically derived material such as collagen, gelatin, chitosan, alginate, a ceramic (with bone-growth enhancers, hydroxyapatite), PEEK (polyether-etherketone), dessicated biodegradable material, metal, composite materials, a biocompatible textile (for example, cotton, silk, linen), extracellular matrix components, tissues, or composites of synthetic and natural materials, or other. Various collagen materials can be used, alone or in combination with other materials, including collagen sutures and threads. Some examples include polymer or collagen threads woven, or knitted, into a mesh. Other suitable materials include thin polymer sheets molded in the presence of a porogen and having underwent leaching; polymer sheets or naturally derived sheets such as fascia and other collagen materials, small intestinal submucosa, or urinary bladder epithelium, the sheets being punctured to introduce porosity; specific shapes printed using available or future printing technologies; naturally secreted materials such as bacterial cellulose grown within specific molds.

In some embodiments, the covering may be formed as a sheet, as a mesh, or in other configurations. In some embodiments, the covering may be a textile type material. Thus, for example, the covering may be formed using a textile approach such as be weaving, rug making, knitting. Such formation may be by a mechanical or industrial method. In another embodiment, a substantially solid sheet may be formed and may be treated to assume a selected implant configuration penetrable by cells, fluids, and proteins. For example, the sheet may be perforated and expand to create openings. In some embodiments, the covering may include a thin sheet that is perforated, expanded to create openings, or otherwise make it penetrable by cells, fluids and proteins in a selected implant configuration.

The foldable covering includes a polymer mesh sheet 12, which has a plurality of foldable walls that include a side 14 and a side 22. In some embodiments, the covering may comprise a mesh material, such as, for example, natural materials, synthetic polymeric resorbable materials, synthetic polymeric non-resorbable materials, and other materials. Natural mesh materials include silk, extracellular matrix (such as DBM, collagen, ligament, tendon tissue, or other), silk-elastin, elastin, collagen, and cellulose. Synthetic polymeric resorbable materials include poly(lactic acid) (PLA), poly(glycolic acid) (PGA), poly(lactic acid-glycolic acid) (PLGA), polydioxanone, PVA, polyurethanes, polycarbonates, polyhydroxyalkanoates (polyhydroxybutyrates and polyhydroxyvalerates and copolymers), polysaccharides, polyhydroxyalkanoates polyglycolide-co-caprolactone, polyethylene oxide, polypropylene oxide, polyglycolide-co-trimethylene carbonate, poly(lactic-co-glycolic acid), and others. See Chen and Wu, "The Application of Tissue Engineering Materials," Biomaterials, 2005, 26(33): p. 6565-78, herein incorporated by reference in its entirety. Other suitable materials include carbon fiber, metal fiber, polyertheretherketones, non-resorbable polyurethanes, polyethers of all types, polyethylene terephthalate, polyethylene, polypropylene, Teflon, and various other meshes. In some embodiments, the covering may comprise non-woven material such as spun cocoon or shape memory materials having a coil shape or shape memory alloys.

In some embodiments, mesh fibers may be treated to impart porosity to the fibers. This may be done, for example, to PLA, PLGA, PGA, and other fibers. One suitable method for treating the mesh fibers comprises supercritical carbon dioxide treatment to partially solubilize the particles. This treatment may further be carried out for viral inactivation. Another suitable method for treating the mesh fibers comprises explosive decompression. Explosive decompression generates porosity and leads to controlled permeability. The mesh material further may be loaded with cells, growth factors, or bioactive agents.

In some embodiments, fibers of a mesh material may be treated such as by having particles adhered thereto. The particles may be, for example, bone particles. Thus, in one embodiment, the covering may comprise a plurality of threads formed into a fabric. The threads may have particles adhered thereto. For example, the threads may have particles strung on the thread. In an alternative embodiment, the covering may be formed of a material and the material may be coated with particles.

Side 14 includes a surface 16, which is configured to receive an agent 20, as described herein. In some embodiments, the agent can include autograft or allograft.

In some embodiments, the agent that is placed in the device can be demineralized bone material (e.g., fibers, chips, powder, or a combination thereof). In some embodiments, the demineralized bone fibers can be elongated and have an aspect ratio of at least from about 50:1 to about at least about 1000:1. Such elongated bone fibers can be readily obtained by any one of several methods, for example, by milling or shaving the surface of an entire bone or relatively large section of bone.

In other embodiments, the length of the fibers can be at least about 3.5 cm and average width from about 20 mm to about 1 cm. In various embodiments, the average length of the elongated fibers can be from about 3.5 cm to about 6.0 cm and the average width from about 20 mm to about 1 cm. In other embodiments, the elongated fibers can have an average length be from about 4.0 cm to about 6.0 cm and an average width from about 20 mm to about 1 cm.

In yet other embodiments, the diameter or average width of the elongated fibers is, for example, not more than about 1.00 cm, not more than 0.5 cm or not more than about 0.01 cm. In still other embodiments, the diameter or average width of the fibers can be from about 0.01 cm to about 0.4 cm or from about 0.02 cm to about 0.3 cm.

In another embodiment, the aspect ratio of the fibers can be from about 50:1 to about 950:1, from about 50:1 to about 750:1, from about 50:1 to about 500:1, from about 50:1 to about 250:1; or from about 50:1 to about 100:1. Fibers according to this disclosure can advantageously have an aspect ratio from about 50:1 to about 1000:1, from about 50:1 to about 950:1, from about 50:1 to about 750:1, from about 50:1 to about 600:1, from about 50:1 to about 350:1, from about 50:1 to about 200:1, from about 50:1 to about 100:1, or from about 50:1 to about 75:1.

In some embodiments, the bone chips can be used and they can be combined with bone fibers, where the chips to fibers ratio is about 90:10, 80:20, 70:30, 60:40, 50:50, 40:60, 30:70, 20:80 and/or 10:90. In various embodiments, a surface demineralized bone chips to fibers ratio is about 90:10, 80:20, 70:30, 60:40, 50:50, 40:60, 30:70, 20:80 and/or 10:90 that can be used in the device. In some embodiments, a surface demineralized chips to fully demineralized fibers ratio is about 90:10, 80:20, 70:30, 60:40, 50:50, 40:60, 30:70, 20:80 and/or 10:90 that can be used in the device.

In some embodiments, the agent can include protein, bone morphogenetic proteins, carbohydrate, lipids, collagen, allograft bone, autograft bone, tricalcium phosphate, hydroxyapatite, growth and differentiation factors, carriers for growth factors, growth factors extracts of tissue, bone marrow aspirate, concentrates of lipid derived or marrow derived adult stem cells, umbilical cord derived stem cells, committed or partially committed cells from osteogenic or chondrogenic lineage, antimicrobials, antibiotics, or combinations thereof.

In some embodiments, the agent includes a bioactive agent or bioactive compound, which includes a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD. A listing of bioactive agents and specific drugs suitable for use with the present disclosure may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996; and the United States Pharmacopeia-25/National Formulary-20, published by the United States Pharmcopeia Convention, Inc., Rockville Md., 2001, each of which is incorporated herein by reference.

In some embodiments, the agent includes elongated bone-derived particles or fragments of small intestinal submucosa combined longitudinally into three small bundles, each having, for example, from about 1 to about 3 tissue particles. The three bundles may then be braided. Various methods of braiding and types of braids any of which may be useful in producing the covering. The ends of the braided tissue-derived particles may then be glued together using a fixation agent to prevent their unraveling, or they may be held together with a biocompatible polymer or metal band.

In some embodiments, bone-derived particles are combined with a solvent to form agent. Exemplary solvents include water, lower alkanols, ketones, and ethers and mixtures of any of these or other materials. The agent may then be extruded at an appropriate temperature and pressure to create a thread. Threads may also be produced by spinning, drawing, rolling, solvent-extruding, cutting or laser cutting from a sheet or bar stock. The agent may alternatively be cast or molded into a solid sheet or bar stock and then cut into thin threads. These may be used immediately or woven into a mesh. Alternatively or in addition, they may be spliced, wrapped, plied, cabled, braided, woven, or some combination of these. The agent may be shaped by thermal or chemical bonding, or both. In some embodiments, a portion of the solvent is removed from the agent before extrusion.

In some embodiments, a thread of a biocompatible natural or synthetic agent, for example, polylactide or collagen, may be coated with tissue-derived or other elements, for example, by dubbing. For example, a polymer fiber may be coated with an adhesive, for example, lecithin, and bone particles or other osteoconductive or osteoinductive fibrils allowed to adhere to the thread. The thread may then be twisted on itself or with a second or a plurality of similarly treated threads. Alternatively or in addition, the threads may be braided. The adhesive may be a lipid that is waxy at room temperature, for example, a di- or tri-glyceride that is solid at room temperature. Alternatively or in addition, the adhesive may be a phosphocholine or phosphatidylcholine. In some embodiments, the adhesive is a material that binds both the thread and the agent that is used to coat the thread (e.g., bone particles) but that does not degrade either. Non-aqueous adhesives may improve the stability of the final aggregate as compared to aqueous adhesives.

The covering shape, mesh size, cable thickness, and other structural characteristics, such as architecture, may be customized for a selected implant configuration, as described herein. For example, where a two dimensional aggregate is used to retain a thixotropic material within a gap, a tight weave is preferred to prevent leakage. To optimize cell or fluid migration through the mesh, the pore size may be optimized for the viscosity and surface tension of the fluid or the size of the cells. For example, pore sizes on the order of approximately 100-200 µm may be used if cells are to migrate through the mesh. Mesh size may be controlled by physically weaving strands of the material by controlling the ratio of solvent to solids in a precursor material.

Cells may be seeded onto an agent, or contained within it. In some embodiments, cells may be encapsulated in a matrix such as alginate or collagen gel and the capsules placed on the agent. Seeded materials generally do not need to be incubated for long periods of time in solutions that could partially dissolve the binding agent. Instead, the capsules may be placed on the agent or covering shortly before implantation. In another embodiment, cells are simply mixed with a gel which is then combined with the agent. Alternatively, an agent or covering may be cultured with cells before implantation. In one embodiment, thicker materials are used for culturing to increase mechanical integrity during implantation. Any class of cells, including connective tissue cells, organ cells, muscle cells, nerve cells, and stem cells, may be seeded onto the spinal implant. In an exemplary embodiment, connective tissue cells such as osteoblasts, osteoclasts, fibroblasts, tenocytes, chondrocytes, and ligament cells and partially differentiated stem cells such as mesenchymal stem cells and bone marrow stromal cells are employed.

The agent may be packed in the covering at any suitable density. For some applications, the agent may be loosely packed in the covering to enhance manipulability. In some embodiments, the agent may be packed in the covering such that the covering retains flexibility and may be folded over itself. In some embodiments, the covering may be configured to facilitate placement of graft material in the covering as described herein.

In some embodiments, the agent may be homogenous or heterogeneous. The agent may be selected to exhibit certain gradients. For example, the agent may be selected to exhibit a gradient to guide, lure, or attract cells along a pathway. Such gradient may comprise a cell gradient, a cell type gradient (for example transitioning from bone cells to cartilage cells or transitioning from bone cells to tendon cells), a gradient of conductivity, or a gradient of density/porosity. In some embodiments, the agent may comprise a sequence of ingredients.

For embodiments wherein the agent is biologic, the agent may be autogenic, allogenic, xenogenic, transgenic, or combinations of these. Each of these tissue types includes any tissue of bone origin, connective tissue origin, or any collagen containing material including organ tissues. Other suitable agent that may be positioned in the covering include, for example, protein, hormones, nucleic acid, carbohydrate, lipids, collagen (autograft, allograft, or xenograft from musculoskeletal or organ systems), allograft bone, autograft bone, cartilage stimulating substances, allograft cartilage, TCP, TCP/calcium sulfate, calcium carbonate, calcium phosphates, bioactive glasses, glass ceramics, magnesium phosphates, phosphates containing any biocompatible metal ion, porous implants of all types including trabecular metal, biocompatible metals including stainless steel, cobalt-chrome, titanium, titanium alloys, polymers such as polylactic acid, polyglycolic acid, polycaprolactone, polyglycolide-co-caprolactone, polyethylene oxide, polypropylene oxide, polyglycolide-co-trimethylene carbonate, poly(lactic-co-glycolic acid), poly-L-lactide, polyethylene glycol, polyetheretherketones, polyurethanes, polyethers of all types, poly ethylene terephthalte, polyethylene, polypropylene, Teflon, chondroitin sulfate, hyaluronic acid and its salts, chitosan and derivatives, natural polymers such as silk, collagen, polysaccharides, polyhydroxyalkanoates, polymers combined with bone or collagen or both from any source (allograft, xenograft, transgenic, autograft), hydroxyapatite, calcium sulfate, polymer, nanofibrous polymers, growth factors, carriers for growth factors, growth factor extracts of tissues, demineralized bone matrix, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, platelets, activated platelets, antibiotics, substances with antimicrobial properties, or combinations of any of the above. In accordance with one embodiment, the agent is a bone matrix composition such as described in U.S. patent application Ser. No. 12/140,044 and U.S. Patent Publications Nos. 2007/0098756 and 2007/0110820 all for Bone Matrix Compositions and Methods, herein incorporated by reference in their entireties. Suitable agent for preparing biocomposites for placement in the covering are disclosed in U.S. Patent Publication Nos. 2007/0191963, 2006/0216323, and 2005/0251267, U.S. Pat. Nos. 6,696,073, 6,478,825, 6,440,444, and 6,294,187, all herein incorporated by reference in their entireties for all purposes.

In some embodiments, the spinal implant may be used in the disc space, between implants, or inside a cage. In some embodiments, the agent may include a natural and/or synthetic expandable material. The expandable material may comprise bone particles, a polymer, a hydrogel, a sponge, collagen, or other material. In various embodiments, the expandable material comprises bone allograft comprising demineralized bone particles, and the demineralized bone particles may be a blend of cortical and cancellous bone. For example, the expandable material may comprise demineralized cortical fibers and demineralized cancellous chips, wherein the demineralized cancellous chips may create a healthy matrix for the incorporation of new bone and add advanced expansion characteristics.

In addition to bone particles, an expandable polymer, a collagen sponge, compressed and/or dried hydrogels, or other materials may be used. In addition to expansion properties, the agent may exhibit osteoinductive and/or osteoconductive properties. For example, cancellous bone particles may exhibit osteoconductive properties while demineralized cortical bone particles may exhibit osteoinductive properties.

In some embodiments, the agent may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; demineralized bone powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin; bacteriaphages; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other means; tissue transplants; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids.

In some embodiments, the bioactive agent may be a drug. In some embodiments, the bioactive agent may be a growth factor, cytokine, extracellular matrix molecule, or a fragment or derivative thereof, for example, a protein or peptide sequence such as RGD. A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996; and the United States Pharmacopeia-25/National Formulary-20, published by the United States Pharmacopeia Convention, Inc., Rockville Md., 2001.

In some embodiments, the drug can be a statin. Examples of a useful statin for treatment of pain and/or inflammation include, but is not limited to, atorvastatin, simvastatin, pravastatin, cerivastatin, mevastatin, velostatin, fluvastatin, lovastatin, rosuvastatin and fluindostatin (Sandoz XU-62-320), dalvastain, eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin. Anti-inflammatory agents also include those with anti-inflammatory properties, such as, for example, amitriptyline, carbamazepine, gabapentin, pregabalin, clonidine, or a combination thereof.

Sheet 12 includes a side 22. Side 22 includes a surface 24, which is configured for connection with surface 16 via connectable surfaces, as described herein. In some embodiments, the connectable surfaces include a hook configuration 26 disposed with surface 24 and a loop configuration 28 disposed with surface 16 to facilitate connection of surfaces 16, 24. In some embodiments, hook and loop configuration 26, 28 comprise Velcro. In some embodiments, the foldable walls of sheet 12 include a plurality of panels 30, 30a and 30b that are folded upon one another such that the covering can be folded into spinal implant 11 in a selected implant configuration. Panels 30 are connected by delineations, such as, for example, fold lines 32.

Surface 24 is connected with surface 16 via connectable surfaces intra-operatively forming a selected implant configuration, as described herein. In some embodiments, sheet 12 is folded to form the selected implant configuration. In some embodiments, the selected implant configuration includes a specific cross section. In some embodiments, the cross section can include, for example, tubular, cylindrical, circular, oval, rectangular and/or square.

In some embodiments, the selected implant configuration has a cross sectional shape selected from generally circular or generally oval and a shape that can be tubular, rectangular, or cubic. In some embodiments, the selected implant configuration of the covering may include an expanded configuration. In some embodiments, expansion can be provided such that the covering expands when placed in the body or the covering may be made of a material that expands when it comes in contact with water or other bodily fluids, either by way of liquid absorption, or by stretching when the materials absorb liquid and expand. In some embodiments, the covering may be substantially non-expandable or minimally deformable.

In some embodiments, the selected implant configuration of spinal implant 11 can include, for example, a cylinder or a bag, whether the covering has a single or a plurality of compartments, and whether the covering includes attachment mechanisms. In some embodiments, the selected implant configuration of spinal implant 11 may be configured to conform to surrounding bony contours of the space in which it is placed.

In some embodiments, the selected implant configuration of spinal implant 11 can include a ring, a cylinder, a cage, a rectangular shape, a mesh, a suture-like wrap, a continuous tube, or other configuration. In some embodiments, the selected implant configuration of spinal implant 11 is designed to fit adjacent to spinal processes for posterolateral spine fusion, a cube like structure designed to fit between vertebral bodies or within cages for interbody spinal fusion, a tube-like shape where the ends are designed to be fitted onto nonunion long bone defects, relatively flat shapes designed to fill cranial or maxillofacial defects, rectangular structures designed for osteochondral defects, structures shaped to fit around various implants (for example, dental, doughnut with hole for dental implants), or relatively elastic ring-like structures that will stretch and then conform to shapes (for example, rubber band fitted around processes). In some embodiments, the selected implant configuration of spinal implant 11 includes a cage, which comprises a plurality of compartments. For example, in a tubular embodiment, the tube may be formed into a plurality of compartments by tying a cord around the tube at one or more points, or by other suitable mechanism such as crimping, twisting, knotting, stapling, sewing, or other. The selected implant configuration of the covering may be determined by the agent to be provided within the covering. For example, if the agent to be contained comprises fibers, the covering may be formed as strings or sutures that are wrapped around the fibers.

In some embodiments, surfaces 16, 24 can be connected by connectable surfaces, such as, for example, a draw string, stitches, sutures, heat seals, adhesion, pressure fittings, coil ring, twist tie or combinations thereof. In some embodiments, the connectable surfaces can be defined by portions of sheet 12, such that manipulation, such as, for example, by folding, bending and/or twisting of sheet 12 forms a closed container in the selected implant configuration.

In some embodiments, agent 20 is disposed with surface 16. Sheet 12 is manipulated intra-operatively, such as, for example, by folding. Sheet 12 is folded such that panel 30 is pivoted and/or rotated, in a direction shown by arrow A in FIG. 2. Sheet 12 is folded such that panel 30b is pivoted and/or rotated, in a direction shown by arrow B in FIG. 2. Panel 30 is folded such that a portion of surface 24 disposed with panel 30 is adjacent and facing a portion of surface 16 disposed with panel 30b. Folding of panels 30, 30b facilitates engagement and fixation of surfaces 16, 24 to dispose the foldable walls of the covering in a selected implant configuration of spinal implant 11.

As panels 30, 30b are manipulated, surface 24 is connectable with surface 16 to fix panels 30, 30a, 30b in the selected configuration, as shown in FIG. 4. In some embodiments, surface 24 can be disengaged from surface 16 to facilitate reconfiguration and/or adjustment of panels 30, 30a, 30b into a new or second revised selected configuration such that the selected configuration is customizable intra-operatively. Upon folding of panels 30, 30b, agent 20 is encased and/or contained by panels 30, 30a, 30b to retain agent 20 therein. Panels 30, 30a, 30b are manipulated to enclose end portions of the selected configuration.

In use, spinal implant system 10, similar to the systems and methods described herein, is employed to treat a selected section of vertebrae V. In some embodiments, spinal implant 11 is employed with vertebrae V at the surgical site during a surgical procedure, such as, for example, a posterolateral fusion, as shown in FIG. 5. A medical practitioner obtains access to a surgical site including vertebrae V in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating a spine disorder.

An incision is made in the body of a patient and a cutting instrument (not shown) creates a surgical pathway for implantation of components of spinal implant system 10 with a portion of vertebrae V including one or more transverse process TP. A preparation instrument (not shown) can be employed to prepare tissue surfaces of vertebrae V.

In some embodiments, sheet 12 and agent 20 are selected based on one or more parameters, such as, for example, patient anatomy, patient disorder, surgical procedure, surgical conditions, intra-operative conditions, modification or strategy and/or practitioner preference. Based on the one or more parameters, sheet 12 includes a first configuration and is manipulated and/or folded into a selected implant configuration intra-operatively to contain agent 20 and comprise spinal implant 11.

Sheet 12 is disposed in a substantially flat or even configuration, as shown in FIG. 1. Agent 20 is disposed with surface 16, as described herein. Sheet 12 is manipulated intra-operatively. Sheet 12 is folded such that panel 30 is pivoted and/or rotated, in a direction shown by arrow A in FIG. 2. Sheet 12 is folded such that panel 30b is pivoted and/or rotated, in a direction shown by arrow B in FIG. 2. Panel 30 is folded such that a portion of surface 24 disposed with panel 30 is adjacent and facing a portion of surface 16 disposed with panel 30b, as shown in FIG. 3. Folding of panels 30, 30b facilitates engagement and fixation of the connectable surfaces of surfaces 16, 24, as described herein, to dispose the foldable walls of the covering in a selected implant configuration of spinal implant 11. As panels 30, 30b are manipulated, surface 24 is connectable with surface 16 to fix panels 30, 30a, 30b in the selected configuration, as shown in FIG. 4. Upon folding of panels 30, 30b, agent 20 is encased and/or contained by panels 30, 30a, 30b to retain agent 20 therein. Panels 30, 30a, 30b are manipulated to enclose end portions of the selected configuration of spinal implant 11.

In the selected implant configuration, as shown in FIG. 5, spinal implant 11 is disposed in a selected orientation with the one or more transverse process TP and/or adjacent portions of vertebrae V at the surgical site in connection with the posterolateral fusion.

In some embodiments, sheet 12 may contain an attachment or coupling mechanism, as described herein, to attach spinal implant 11 to skeletal or soft tissue proximate to a surgical site. In some embodiments, the attachment mechanism can include a tab, loop, tack or a hook-and loop (Velcro) portion.

In some embodiments, the attachment mechanisms may provide for attachment to other coverings, or for attachment to adjacent implantable medical devices or products (such as a rod or screw or cross-brace of a pedicle screw fixation system, a hip prosthesis, a bone plate, and the like). In some embodiments, the attachment mechanisms may provide for attachment to bone or to adjacent tissues such as muscle, tendon, or ligament. Chemical attachment mechanisms may comprise, for example, a bioadhesive or glue, cement, tape, tissue adhesives, or similar mechanism. Chemical attachment mechanisms may further comprise mechanisms that facilitate cross-linking. In some embodiments, attachment mechanisms such as crimping, welding, soldering, or brazing may be used. Further, attachment may be achieved via friction. In some embodiments, biological attachment may be via mechanisms that promote tissue ingrowth such as by a porous coating or a hydroxyapatite-tricalcium phosphate (HA/TCP) coating.

In some embodiments, spinal implant system 10 comprises a kit including a plurality of alternate implants 11, similar to that described herein. In some embodiments, spinal implant system 10 can include one or a plurality of fasteners such as those described herein and/or fixation elements, which may be employed with a single vertebral level or a plurality of vertebral levels. In some embodiments, the fasteners may be engaged with vertebrae in various orientations, such as, for example, series, parallel, offset, staggered and/or alternate vertebral levels. In some embodiments, the fasteners may be configured as multi-axial screws, sagittal angulation screws, pedicle screws, mono-axial screws, uni-planar screws, fixed screws, anchors, tissue penetrating screws, conventional screws, expanding screws. In some embodiments, the fasteners may be employed with wedges, anchors, buttons, clips, snaps, friction fittings, compressive fittings, expanding rivets, staples, nails, adhesives, posts, connectors, fixation plates and/or posts.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method for treating a spine, the method comprising the steps of:
    disposing an agent with a covering that includes a first surface and a second surface; the covering comprising a first panel having an outer face formed from the second surface, a second panel, and a third panel having an inner face formed from the first surface;
    intra-operatively folding the covering such that the outer face of the first panel is connected with the inner face of the third panel in a selected implant configuration; and
    connecting the selected implant configuration with tissue, wherein the covering comprises a biodegradable polymer.

2. A method as recited in claim 1, wherein the tissue includes at least one transverse process of a spine.

3. A method as recited in claim 1, wherein the first surface is covered by loops and the second surface is covered by hooks.

4. A method as recited in claim 1, wherein the covering is foldable between a flat configuration and a selected implant configuration.

5. A method as recited in claim 1, wherein a first side of the covering has the first surface to dispose the agent thereon and a second side of the covering has the second surface.

6. A method as recited in claim 1, wherein the first, the second and the third panels are connected by fold lines.

7. A method as recited in claim 1, wherein the covering comprises a porous mesh.

8. A method as recited in claim 1, wherein the first and the second surfaces are connectable via a hook and loop configuration.

9. A method as recited in claim 1, wherein the selected implant configuration of the covering includes a cross sectional shape selected from generally circular or generally oval.

10. A method as recited in claim 1, wherein the selected implant configuration of the covering includes a shape selected from tubular, rectangular, cube or mesh bag.

11. A method as recited in claim 1, wherein the agent comprises autograft or allograft.

12. A method as recited in claim 1, wherein the agent comprises demineralized bone matrix comprising particles and fibers of demineralized bone.

13. A method as recited in claim 1, wherein the agent comprises demineralized bone matrix fibers and demineralized bone matrix particles in a 30:70 ratio.

14. A method as recited in claim 1, wherein the agent comprises bone morphogenetic protein.

15. A method for treating a spine, the method comprising the steps of:
    disposing an agent including autograft with a foldable polymer mesh sheet that includes a first surface and a second surface, the foldable polymer mesh sheet comprising a first panel having an outer face formed from the second surface, a second panel, and a third panel having an inner face formed from the first surface;
    intra-operatively folding the foldable polymer mesh sheet such that the outer face of the first panel is connected with the inner face of the third panel in a selected implant configuration; and
    connecting the selected implant configuration with tissue.

16. A method as recited in claim 15, wherein the foldable polymer mesh sheet is configured to form a folded configuration such that the agent is contained completely within the spinal implant.

* * * * *